United States Patent [19]

Cerami et al.

[11] 4,371,374
[45] Feb. 1, 1983

[54] MONITORING METABOLIC CONTROL IN DIABETIC PATIENTS BY MEASURING GLYCOSYLATED AMINO ACIDS AND PEPTIDES IN URINE

[75] Inventors: Anthony Cerami, Flanders, N.J.; Michael Brownlee; Helen Vlassara, both of New York, N.Y.

[73] Assignee: The Rockefeller University, New York, N.Y.

[21] Appl. No.: 207,471

[22] Filed: Nov. 17, 1980

[51] Int. Cl.$^3$ .................................................. G01N 33/50
[52] U.S. Cl. .................................. 23/230 B; 422/56; 422/57; 422/61
[58] Field of Search .................. 23/230 B, 901, 913; 422/61, 57, 56

[56] References Cited

U.S. PATENT DOCUMENTS 4,235,601 11/1980 Deutsch et al. ........................ 422/56
4,269,605 5/1981 Dean et al. ............................ 23/901

OTHER PUBLICATIONS

Bisbee et al., *A Method for Measuring Hydroxylysine and Glycosylated Hydroxylysines in Urine and Protein Hydrolysates,* Clinica Chimica Acta, 90, (1978), 29–36.
R. J. Koenig and A. Cerami: "Synthesis of Hemaglobin A$_{1c}$ in Normal and Diabetic Mice: Potential Model of Basement Membrane Thickening: Proc. Nat. Acad. Sci. 72 at 3,687–3,691, (1975).
F. J. Stevens, H. Vlassara, A. Abati, and A. Cerami: "Non-Enzymatic Glycosylation of Hemoglobin", J. Biol. Chem. 252 at 2,998–3,002, (1977).
V. M. Monnier and A. Cerami: "Nonenzymatic Browning in Vivo: Possible Aging Process of Long-Lived Proteins", Science 211 at 491–493, (1981).
M. Brownlee, H. Vlassara, and A. Cerami: "Measurement of Glycosylated Amino Acids and Peptides from Urine of Diabetic Patients Using Affinity Chromatography", Diabetes 29 at 1,004–1,047, (1980).
R. J. Koenig, V. J. Stevens, and A. Cerami: "Non-Enzymatic Glycosylation and Browning of Hemoglobin and Other Body Proteins", J. Applied Biochem. 2 at 431–438, (1980).
CLINISTIX ® Reagent Strips for Urinalysis, Ames Division, Miles Laboratories, Inc., 1979, (Revised 5/81).
CLINITEST ® 2-Drop Method for the Quantitative Determination of Reducing Sugars in Urine, Ames Division, Miles Laboratories, Inc., 1979, (Revised 4/81).
CLINITEST ® 2-Drop Method using Ames CLINITEST Reagent Tablets for the Quantitative Determination of Reducing Sugars in Urine, Ames Division, Miles Laboratories, Inc., 1979, (Revised 11/80).

*Primary Examiner*—Peter Chin
*Attorney, Agent, or Firm*—Oblon, Fisher, Spivak, McClelland & Maier

[57] ABSTRACT

A method of monitoring metabolic control in a diabetes patient comprising measuring the amount of non-enzymatic glycosylated amino acids and peptides in urine of the patient; a method of measurement and a test kit for the measurement are disclosed.

26 Claims, 10 Drawing Figures

MONITORING METABOLIC CONTROL IN DIABETIC PATIENTS BY MEASURING GLYCOSYLATED AMINO ACIDS AND PEPTIDES IN URINE

BACKGROUND OF THE INVENTION

1. Field of the Invention

This invention relates to a method for separating and quantitating the degradation products of non-enzymatic glycosylated proteins.

2. Description of the Prior Art

Glucose has been found to covalently modify a variety of proteins non-enzymatically in vivo, including hemoglobin, crystallins of lens protein, serum albumin and erythrocyte cell membrane. (Koenig et al, "Correlation Of Glucose Regulation And Hemoglobin $A_{1C}$ In Diabetes Mellitus", N. Engl. J. Med., 295, 417–420 (1976); Stevens et al, "Diabetic Cataract Formation: Potential Role Of Glycosylation Of Lens Crystallins", Proc. Natl. Acad. Sci. U.S.A., 75, 2918–2922 (1979); Day et al, "Non-enzymatically Glucosylated Albumin", J. Biol. Chem. 254, 595–597 (1979); and Miller et al, "Non-enzymatic Glycosylation Of Erythrocyte Membrane Proteins", J. Clin. Invest., 65, 896–901 (1980)). This non-enzymatic glycosylation reaction most probably occurs with other proteins of the body as well, particularly in the insulin-independent tissues of diabetic patients (Cerami et al, "Role Of Non-enzymatic Glycosylation In the Development Of The Sequelae Of Diabetes Mellitus", Metabolism, 28, 431–437 (1979)). The concentration of glycosylated hemoglobin has been shown to reflect mean blood glucose concentration during the preceding several weeks, and has thus provided an important new measurement for monitoring metabolic control in diabetic patients. The utility of this indicator in out-patient management of diabetes is somewhat limited, however, by the impracticality of making this measurement at frequent intervals at home, i.e. the taking of blood samples on a regular basis.

Additionally various techniques have been developed in the prior art for testing for proteinaceous materials, glucose and blood sugar conditions. Atkinson et al., U.S. Pat. No. 3,438,737, discloses a test for proteinaceous materials in various fluids, including urine, using a chromogenic indicator taking advantage of the so-called "protein error" phenomena. However, there is no indication that the proteinaceous materials are glycosylated amino acids and proteins, let alone that the test is more specific than "proteins". Haack et al., U.S. Pat. No. 3,443,903, discloses, very generally, test papers for the detection of glucose, proteins and the like in biological fluids such as urine. There is no suggestion of a test for glycosylated amino acids and peptide. Acuff, U.S. Pat. Nos. 4,168,147; 4,142,856; 4,142,857; and 4,142,858, discloses methods for determining the blood sugar condition of diabetes patients by measuring the level of a specific hemoglobin species, $Hb\text{-}A_{1a\text{-}c}$, in whole blood. There is no suggestion of testing urine.

A need therefore continues to exist for a method for monitoring metabolic control in diabetic patients which is practical for home use in the management of outpatients.

SUMMARY OF THE INVENTION

Accordingly, one object of the invention is to provide a method for monitoring metabolic control in diabetic patients which is practical for out-patient management.

Another object of this invention is to provide a method for the measurement of the degradation products of non-enzymatically glycosylated proteins.

Another object of this invention is to provide a test kit for the measurement of the degradation products of non-enzymatically glycosylated proteins in urine.

Briefly, these objects and other objects of the invention as hereinafter will become more readily apparent can be attained by providing a method for separating and quantitating the degradation products of non-enzymatic glycosylated proteins.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
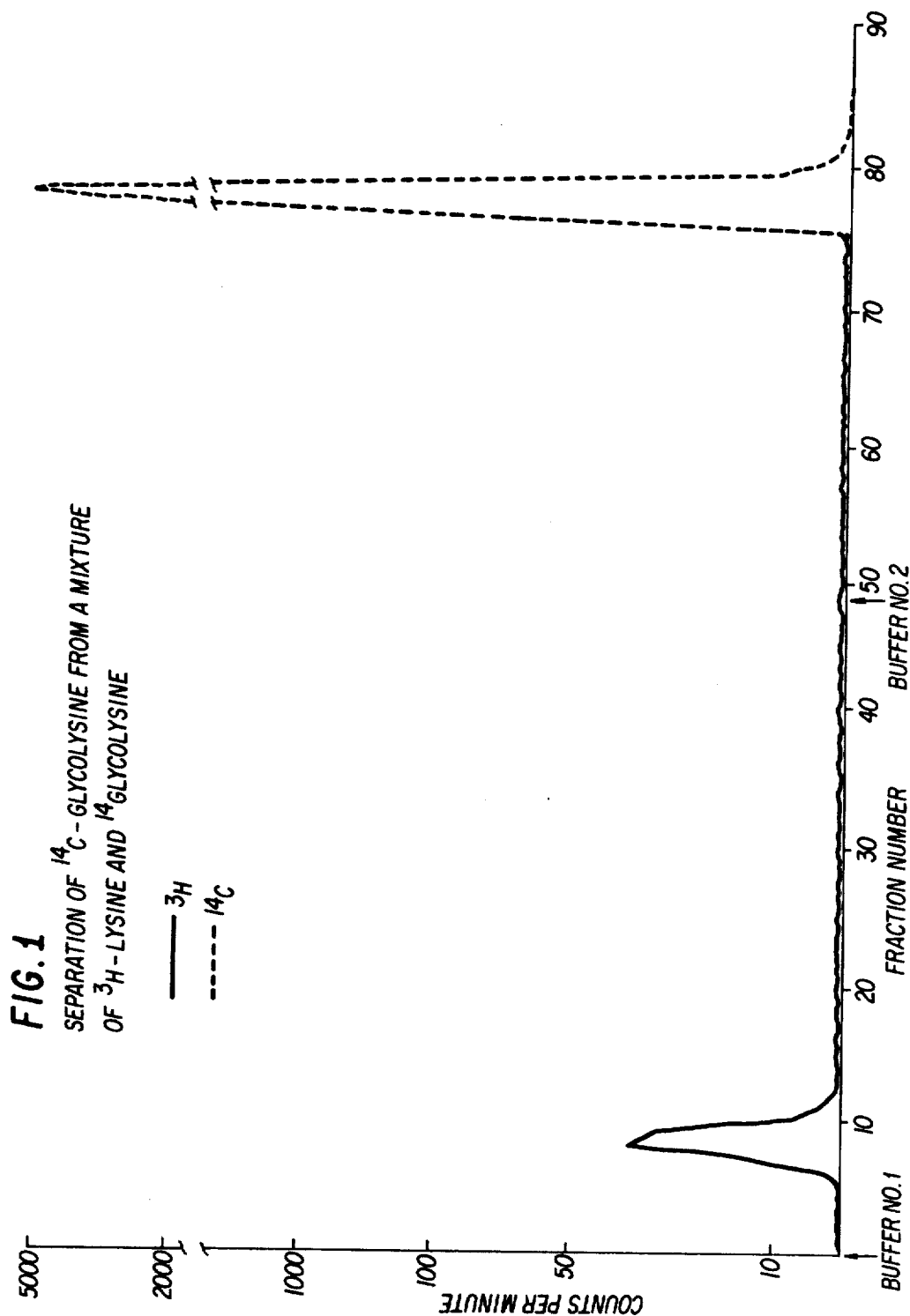
FIG. 1 is a plot showing the separation of $^{14}C$-glycosylated lysine from a mixture of $^{3}H$-lysine and $^{14}C$-glycosylated lysine.

This invention relates to the measurement of glycosylated amino acids and/or peptides in urine, by separating and quantitating these compounds. This assay reflects changes in metabolic control, since it measures degradation products of glycosylated proteins. As previously noted, the concentration of non-enzymatically glycosylated proteins in blood has been shown to reflect mean blood glucose concentration during the preceding several weeks. Also, as previously noted, glycosylation of numerous other proteins occurs in the body. It has now been found that the metabolic degradation productions of these proteins, i.e. non-enzymatically glycosylated amino acids and peptides, also reflect the mean blood glucose concentration. This in itself, is surprising since enzymatically glycosylated proteins which are broken down by the body do not appear as glycosylated peptides or amino acids in the urine or appear in such small quantities and relatively constant concentrations as to have no affect on the technique of this invention. It is the discovery that the degradation products of non-enzymatically glycosylated proteins appear as glycosylated amino acids and/or peptides in the urine which forms the basis of this invention.

In contrast to the testing of urine for sugar level, which is indicative of glucose levels over only a few hours preceding the test; the technique of this invention, quantitation of the non-enzymatically glycosylated amino acid and peptides, provides a reflection of the integrated glucose concentration over the period of about one week to one month preceding the test. Accordingly, by separating and quantitating the non-enzymatically glycosylated amino acids and peptides found in urine, it is possible to obtain an accurate reflection of the integrated mean glucose concentration. Furthermore, this method is readily adaptable to many clinical environments since it involves only urine sampling. In particular, the method is not only readily useable in the hospital laboratory, but is also readily used for outpatient services and in the office of the treating physician.

The method is also based on the observation that boronic acids in alkaline solution form specific complexes with the coplanar cis-diol groups of fructose (Ferrier, R. J., "Carbohydrate Boronates", Adv. Carb. Chem. Biochem., 35, 31–80 (1978)). Since the stable forms of non-enzymatic glycosylation products are known to be 1-deoxyfructosyl-derivatives of ε-amino groups of lysine and 2-amino groups of N-terminal amino acids (Koenig et al, "Structure Of Carbohydrate Of Hemoglobin $A_{1C}$", J. Biol. Chem., 252, 2992–2997 (1977)),. boronic acids are utilized to specifically retain glycosylated amino acids and/or peptides. Preferably, the boronic acids are immobilized on a support so as to effect complex formation and separation simultaneously. However, the free boronic acids may also be used for complex formation followed by separation by contacting the complex with a suitable support, e.g., o-(carboxymethyl) cellulose which has been converted into the acyl azide will react with an aminophenyloboronic acid complex. The principle of the adsorption is illustrated by the following equations using a phenyl boronic acid:

tides. The cyclic anhydrides of such acids are also suitable, as are more complex boronates. A preferred group of the boronic acids are the arylboronic acids corresponding to the formula

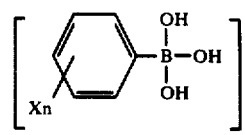

wherein X is at least one member selected from the group consisting of amino, substituted amino, alkyl, halo and hydroxy and n is an integer of from 1 to 5.

In order to facilitate separation of the non-enzymatically glycosylated amino acids and/or peptides complexed with the boronic acids from the urine sample, the boronic acid is immobilized on a support either before or after complex formation. In other words, the boronic acid may be initially immobilized on a support and then contacted with the non-enzymatically glycosylated amino acids and/or peptides, thereby separating these amino acids and/or peptides from solution; or the boronic acid in free form may be contacted with the non-enzymatically glycosylated amino acids and/or peptides and then immobilized, thereby effecting separation of the complex.

Any suitable support, conventionally used for the immobilization of boronic acids, is useable in this invention. Illustrative of such supports are plastics or polymers, e.g. polyacrylamide, cellulose or cellulose derivatives, e.g., paper, carboxymethylcellulose, aminoethylcellulose, etc., or glass, e.g. glass beads.

The amount of the boronic acid used is not critical, so long as sufficient material is provided to complex with all the non-enzymatic glycosylated amino acids and/or peptides. This amount is readily determinable based on the sample aliquot size to be tested and a knowledge of

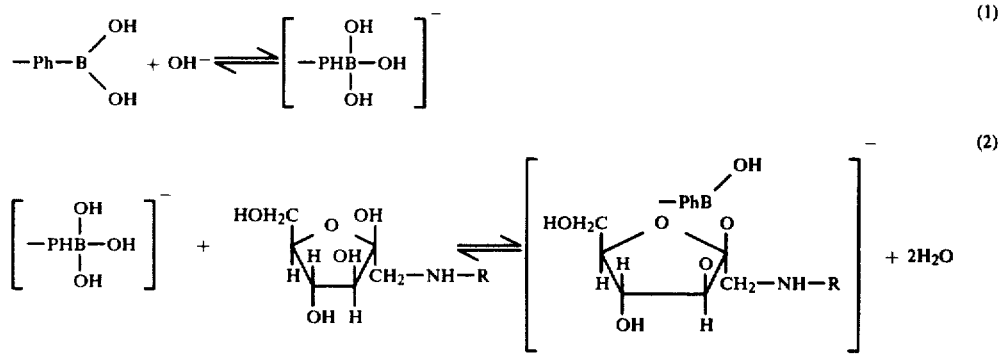

wherein Ph is a phenyl group and R is the remainder of the amino acid or peptide. Preferably, the pH is at least 9 during complex formation. Likewise, lowering the pH by treatment with an acid, e.g., HCl, will drive the equilibrium to the left thereby liberating the non-enzymatically glycosylated amino acid or peptide from the complex with the arylboronic acid. Quantitation may then be achieved by use of any conventional amino acid assay.

Suitable boronic acids include any boronic acid having two acid hydrogen atoms available for complex formation with the coplanar cis-diol groups of the non-enzymatically glycosylated amino acids and/or pepthe expected limits of concentration. Typically, about 5–50 grams of a supported boronic acid (support + acid) are suitable for use with an aliquot (about 0.5%) of a 24 hour urine sample.

After separation of the complex (insolubilized boronic acid complexed with the non-enzymatically glycosylated amino acids and/or peptides) by conventional liquid-solid separation techniques, e.g., filtration, the complex can then be directly analyzed for amino acid content; or the complex can be broken by acidification, followed by separation of the immobilized boronic acid, e.g., by filtration, and analysis of the filtrate for amino acid content.

Many methods for amino acid quantitative analysis exist, e.g., the Millon reaction (tyrosine), Xanthoproteic reaction (tyrosin, tryptophan, phenylalanine), Hopkins-Cole reaction (tryptophan), Ehrlich reaction (tryptophan), Sakaguchi reaction (arginine), Nitroprusside reaction (cysteine), Sullivan reaction (cysteine), Pauly reaction (histidine, tyrosine), Folin-Ciocalteu reaction (tyrosine), ninhydrin reaction ($\alpha$- and $\epsilon$-amino groups), and these are all applicable to the present invention. While many of these tests exhibits specificity for certain amino acids the methods are completely applicable, since urine is a highly heterogeneous mixture of amino acids.

In view of simplicity of operation, color dye reactions, analogous to the Pauly reaction (diazotizied sulfanilic acid), are especially effective in that they can be carried out directly on the complex. Azo dyes are especially suitable, e.g., "dabsyl chloride" (4-dimethylamino azobenzene 4'-sulfinyl chloride). Other useful color reactions may also be used, e.g., "dansyl chloride" (1-dimethylamino naphthalene-5-sulfonyl chloride) which detects amino groups, alkyl and aryl isothiocyanates, e.g. phenylisothiocyanate, various sulfonyl chlorides can covalently react with amino groups which can be quantitated.

Preferably, the color dye reaction is carried out prior to complex formation, since the attached chromophore will not interfere with complex formation, attachment of the chromophore occurring at sites other than the non-enzymatically glycosylated sugar.

In general, Applicants' method comprises separating the non-enzymatically glycosylated amino acid and/or peptides from a urine sample and then quantitating the so-separated material. More particularly, separation is achieved by selective complexation of the non-enzymatically glycosylated amino acids and/or peptides in the urine. Preferably, such complexation is achieved by treatment with immobilized boronic acids under alkaline pH conditions. The amount of the non-enzymatically glycosylated amino acids and/or peptides is then assayed by standard tests for amino acid content. The results of this assay which is reflective of the integrated blood glucose concentration, can then be used by the clinician to determine appropriate modes of therapy, e.g., insulin, diet, exercise, etc., for the diabetic patient.

The method of this invention is readily facilitated by the provision of a test kit comprising an insolubilized boronic acid and a color dye reactive with amino acids. In particular, the insolubilized boronic acid and the color dye are enclosed in separate packets within the kit. Any means of packaging may be used, so long as the two materials are kept separate until combination of the same is desired. Preferably, the insolubilized boronic acid is equilibrated with an alkaline buffer prior to packaging. Preferably, the color dye reactive with amino acids is an azo dye, e.g., diazotized sulfanilic acid or 4-dimethylamino azobenzene 4-sulfinyl chloride, or "dansyl chloride" (1-dimethylamino naphthalene-5-sulfonyl chloride).

Figure 6A:
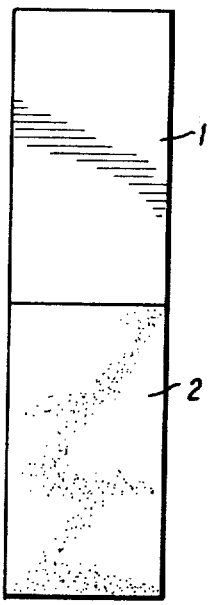
FIG. 6 is a representation of a test strip wherein (a) is a front view and (b) is a side view.
Figure 6B:

The preferred form of the test kit comprises a test strip or test stick and a dye packet. The test strip, illustrated in FIG. 6, comprises a strip of porous material (1) upon which has been coated the boronic acid (2). The strip of porous material can be any material which is inert to the test conditions. Particularly preferred materials are those previously described as being capable of immobilizing boronic acids, thereby allowing direct immobilization of the boronic acid on the strip. Alternatively, an immobilized boronic acid may be coated on the strip.

Figures 7A, 7B:
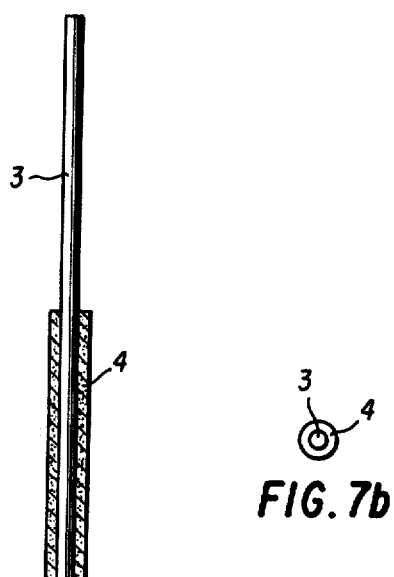
FIG. 7 is a representation of a test stick where (a) is a side view and (b) is an end view.

Likewise, the test stick, illustrated in FIG. 7, may be formed of the same porous materials (3) on which the same boronic acid materials (4) have been coated. While the figure illustrates a circular cross-section, any suitable cross-section can be used.

Figure 8:
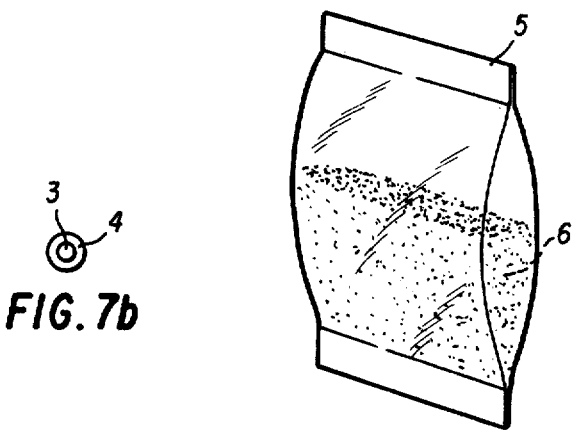
FIG. 8 is a representation of a dye packet.

FIG. 8 illustrates a dye packet for use in the test kit of this invention, however, any suitable packaging means may be used. Typically an envelope (5) is used to contain the dye (6).

Sufficient dye is provided so as to be in at least stoichiometric excess of that necessary to react with all of the amino acids present in the urine sample to be tested.

Sufficient boronic acid is provided so as to be in at least stoichiometric excess of that necessary to form a complex with the non-enzymatically glycosylated amino acids and peptides present in the urine sample.

While there is some variation as to total amino acid content of a urine sample, those skilled in the art can readily determine the stoichiometric amount of dye to be used. Additionally, the non-enzymatically glycosylated amino acid and/or peptide content is subject to variation, e.g., from about 24 to 48 or higher $\mu$moles leucine equivalent/24 hrs/kg of body wt., however, those skilled in the art can readily determine the stoichiometric amount of boronic acid to be used.

The most preferred form of the test kit comprises a test strip which has been at least partially coated with a boronic acid and then impregnated with a color dye reactive with amino acids. Suitable amounts of the component materials are as described above. The same materials and techniques for production of the test strip, described above, can be used with the additional step of impregnating the test strip with the dye. By this technique, a urine sample may be assayed by contacting a pH adjusted urine sample with the test strip, washing the test strip free of non-complexed compounds and non-reacted dye, and then colorimetrically comparing the strip with previously prepared standards.

The methodology of use of the test kit is quite simple. First a urine sample, previously adjusted to an alkaline pH, is reacted with the appropriate dye and then, second, the colored solution is brought into contact with the insolubilized boronic acid. Third, the boronic acid is washed free of non-complexed compounds and non-reacted dye with an alkaline buffer. The remaining colored insolubilized boronic acid complex can then be colorimetrically compared with previously prepared standards to determine the non-enzymatically glycosylated amino acid and/or peptide concentration.

Having generally described this invention, a further understanding can be obtained by reference to certain specific examples which are provided herein for purposes of illustration only and are not intended to be limiting unless otherwise specified.

The following procedure was utilized, unless otherwise specified, in the following examples. Aliquots of samples (0.54% of a 24 hour urine sample) were adjusted to pH 9.0 by adding 0.1 M NaOH. After this pH adjustment the sample was shaken for 30 seconds on a vortex and then centrifuged (5 minutes, 12,000$\times$g) to remove insoluble material. The supernatant fluid was then transferred to the top of a 1.5$\times$14 cm boronate column previously equilibrated with 0.025 M sodium phosphate buffer, pH 9.0, made 1.0 mM with NaN$_3$. The sample was allowed to flow through the column until the liquid meniscus reached the top of the gel bed. Fresh buffer was then applied to the column and 4.0 ml fractions were collected at a flow rate of 20 ml per hour. After 100 fractions were collected, the buffer was removed and the column was eluted with 0.025 M HCl. Fractions (2.0 ml) were collected at a flow rate of 20 ml per hour. Aliquots (400λ) from each fraction were assayed for the presence of ninhydrin-positive material, using the method of Moore and Stein ("A Modified Ninhydrin Reagent For The Photometric Determination Of Amino Acids And Related Compounds", J. Biol. Chem., 211, 907–913 (1954)). Each peak was integrated by weighing to determine the relative amount of ninhydrin-positive material present. The boronate column used comprised m-aminophenyl boronic acid immobilized on Bio-Gel P-6 (Affi-Gel 601, Bio-Rad Laboratories-Richmond, California).

EXAMPLE 1

A synthetic mixture of $^{14}$C-glycosylated lysine (hydrolyzed N$^6$-1-(1-deoxyglucitoyl) N$^2$-t-butoxycarbonyl-lysine—a gift from Dr. Victor Stevens) and $^3$H-lysine (New England Nuclear-Boston, Mass.) was prepared. When the synthetic mixture of radioactive standards was analyzed, the vortex and centrifugation steps were omitted. Aliquots were counted in 7.0 ml hydrofluor (National Diagnostics-Somerville, N.J.), in a Packard liquid scintillation counter. The results are shown in FIG. 1, wherein synthetic $^{14}$C-glycosylated lysine was specifically and completely separated from a mixture of the $^{14}$C-glycosylated lysine and unmodified $^3$H-lysine, demonstrating that breakdown products of non-enzymatically glycosylated proteins would be specifically adsorbed to the column.

EXAMPLE 2

Twenty-four hour urine samples were collected from six normal volunteers and six unselected juvenile-onset diabetic patients. Toluene (10 ml) was added as a preservative during the collection period. Aliquots not analyzed immediately were frozen and stored at −70° C.

Figure 2:
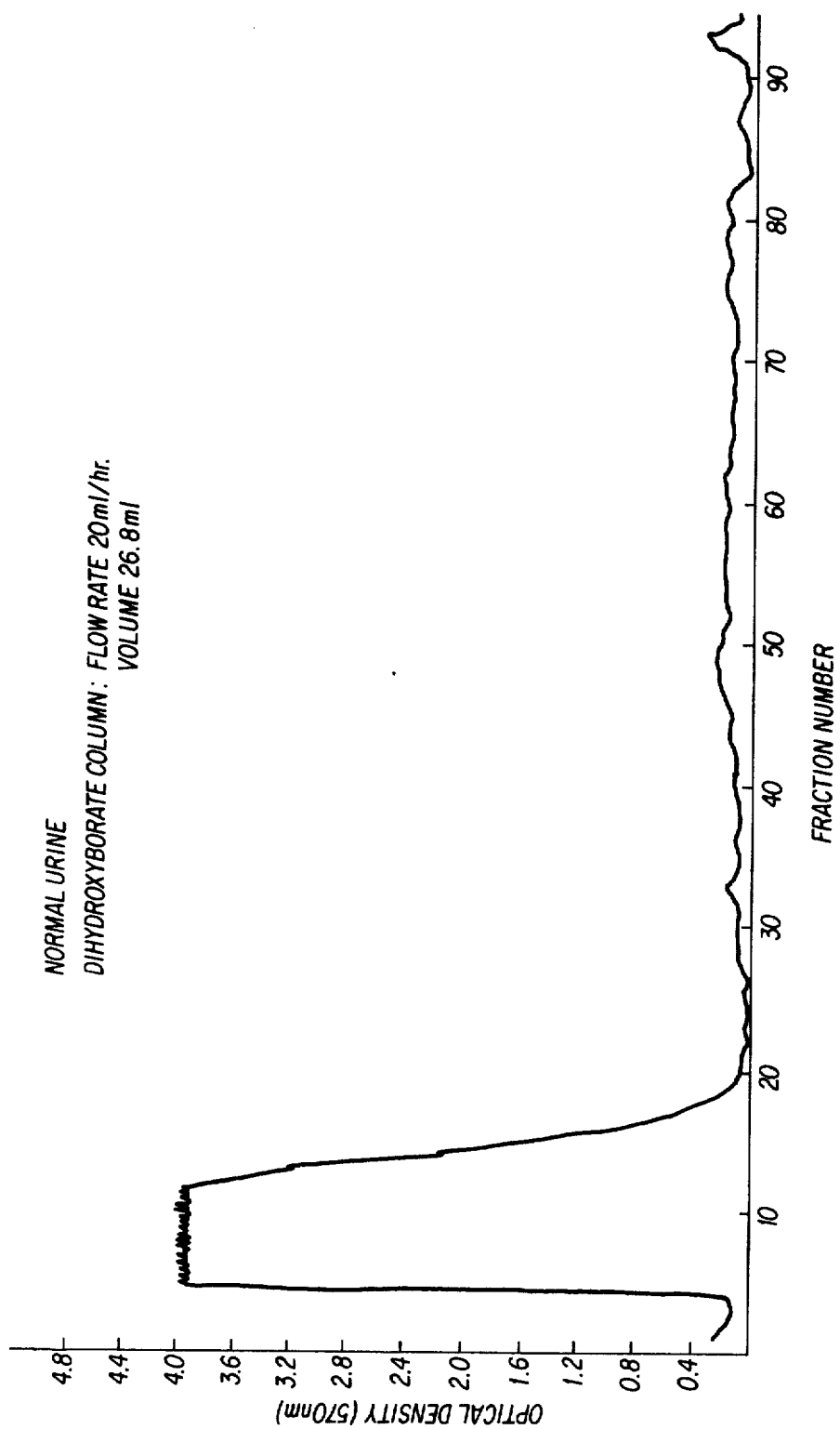
FIG. 2 is a plot showing the elution of a large peak of ninhydrin-positive material in the void volume for urine samples using an alkaline buffer.
Figure 3:
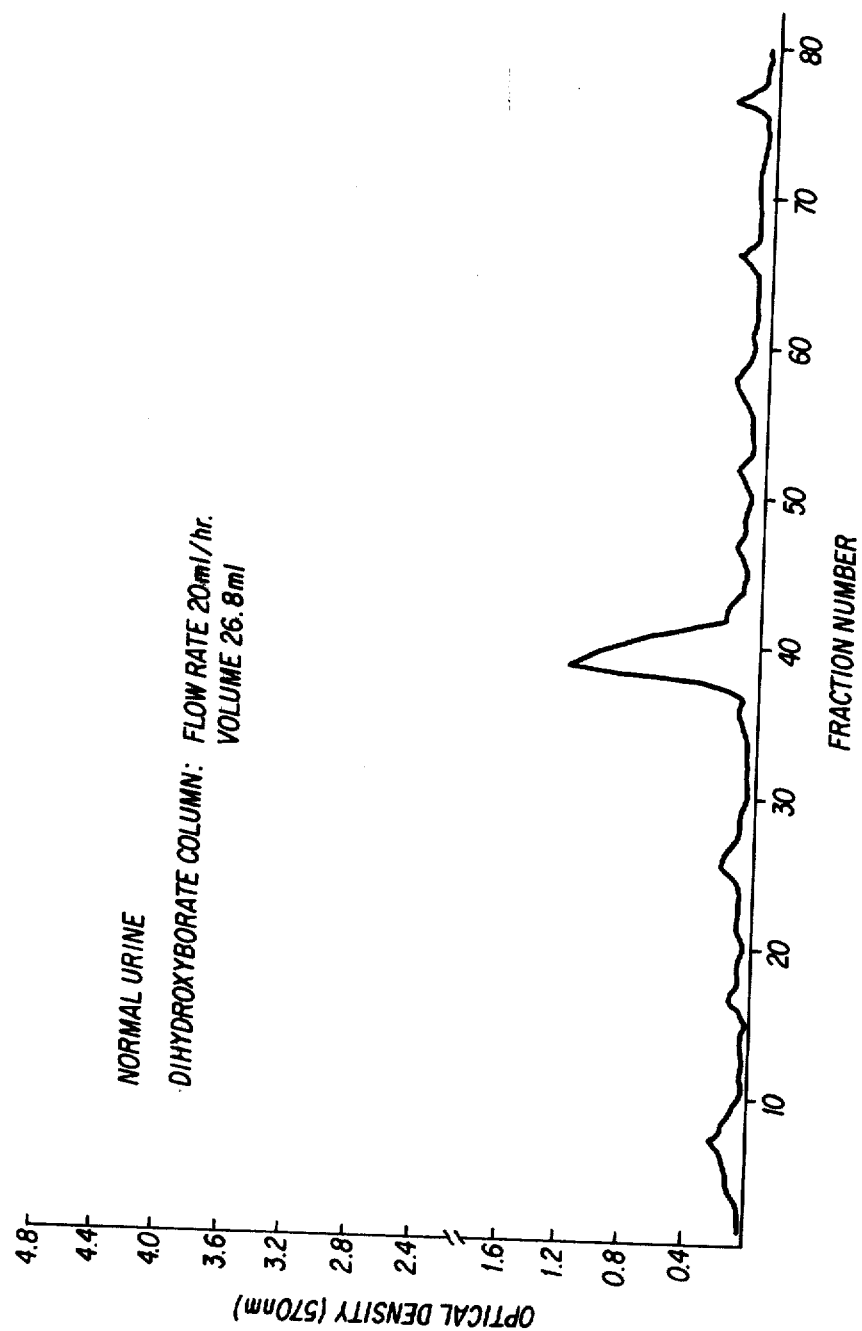
FIG. 3 is a plot showing the elution of a single peak of ninhydrin-positive material, after alkaline washing, for urine samples eluted with HCl.

All urine samples gave essentially identical chromatograms. Washing the column with pH 9.0 sodium phosphate buffer produced a large peak of ninhydrin-positive material in the void volume (FIG. 2). After washing the column with 12 column volumes of buffer, changing to 0.025 M HCl resulted in the elution of a single peak of ninhydrin-positive material (FIG. 3). Since the material in this latter peak must contain both a glycosylated amino group (to be retained on the column) and an unsubstituted amino group (to react with ninhydrin), it represents a mixture of free glycosylated lysine and small peptides containing glycosylated lysine.

Figure 4:
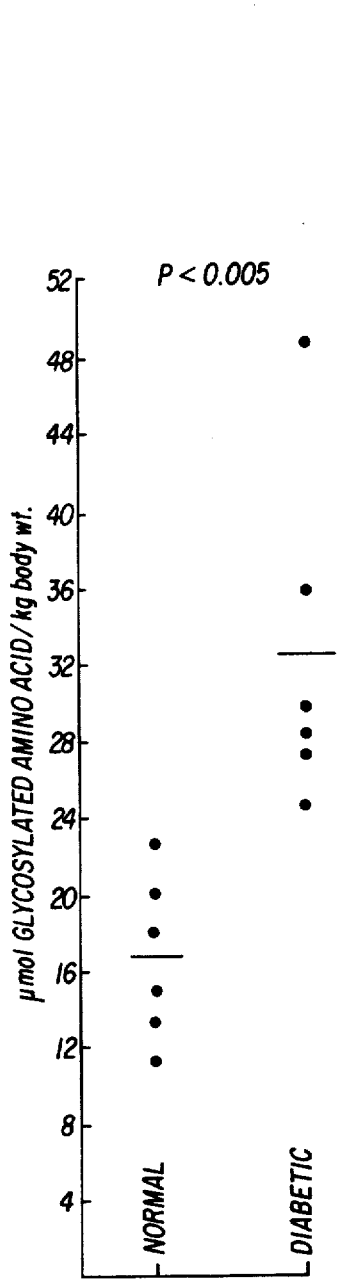
FIG. 4 is a comparison of the levels of degradation products of non-enzymatic glycosylated proteins in urine from diabetic and normal patients.

Comparison of the level of these compounds in urine from diabetic and normal patients shows that the mean level in diabetics is two times that found in urine from normal subjects (FIG. 4). These results show that the measurement of glycosylated proteins or peptides in the urine by this method provides a practical means of monitoring metabolic control in diabetic patients at frequent intervals at home.

EXAMPLE 3

Human diabetic hemoglobin was prepared by the method of Koenig et al (J. Biol. Chem., 252, 2992–2997 (1977)). Hemoglobin (25 mg) was reacted with tritiated sodium borohydride according to the procedure of Bookchin et al ("Structure Of Hemoglobin A$_{1C}$: Nature Of The N-Terminal β-Chain Blocking Group", Biochem. Biophys. Res. Commun., 32, 86–93 (1968)), except that dialysis time was reduced to 24 hours. Globin samples were hydrolyzed in 6 N HCl in sealed tubes at 105° C. for 16 hours. After pH adjustment to 9.0, globin hydrolysates were applied to the previously described boromate columns. Aliquots (200λ) from each fraction were counted in 7.0 ml of hydrofluor, in a Packard liquid scintillation counter. Peak tubes from the HCl column elution were pooled and concentrated. Samples were applied to a Beckman Model 119C amino acid analyzer with stream division (90% to the fraction collector, 1.0 ml fractions) and aliquots (500λ) were counted in 7.0 ml of hydrofluor. The elution patterns were compared with chromatograms of reduced, hydrolyzed glycosylated valine and reduced, hydrolyzed glycosylated lysine standards. The chromatographic pattern of hydrolyzed diabetic hemoglobin previously reduced with NaB$^3$H$_4$ showed a peak of non-specific radioactivity in the void volume (non-glycosylated compounds) and a single sharp peak of radioactivity eluting subsequently with HCl. Amino acid analysis of this latter peak showed that reduced glycosylated valine and reduced glycosylated lysine in approximately equimolar amounts were the only adducts present in the pooled HCl peak. These findings are in agreement with previously published data obtained using other methodologies (Bunn et al, "Structural Heterogeneity Of Human Hemoglobin A Due To Non-Enzymatic Glycosylation", J. Biol. Chem., 254, 3892–3898 (1979) and Gabbay et al, Glycosylated Hemoglobins: Increased Glycosylation Of Hemoglobin A In Diabetic Patients", Diabetes, 28 337–340 (1979)).

EXAMPLE 4

Figure 5:
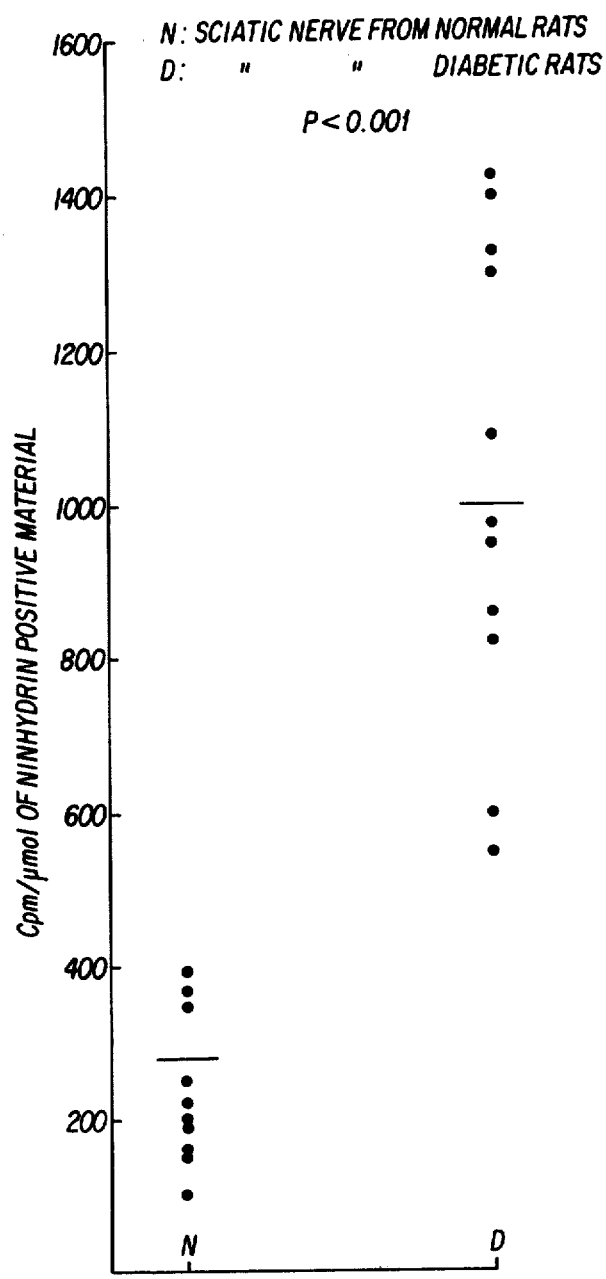
FIG. 5 is a comparison of the levels of non-enzymatically glycosylated amino acids found in the peripheral nerve of normal and diabetic rats.

Using the procedure of Example 3, the peripheral (sciatic) nerve of normal and diabetic rats were analyzed for the amount of non-enzymatic glycosylated amino acids. The nerves were removed, reduced with sodium borohydride, acid hydrolyzed and put on the boronate column as described previously. The results are shown in FIG. 5, expressed as counts per minute (cpm) per micromole of ninhydrin positive material.

Having now fully described this invention, it will be apparent to one of ordinary skill in the art that many changes and modification can be thereto without departing from the spirit or scope of the invention set forth herein.

What is claimed as new and intended to be covered by Letters Patent is:

1. A method of monitoring blood glucose integrated over a period of time from about one week to about one month, separating and quantitating non-enzymatic glycosylated amino acids, peptides or mixtures thereof present in the patient's urine, comprising:
   (a) treating a urine sample containing said non-enzymatic glycosylated amino acids, peptides or mixtures thereof with a suitable boronic acid to form a complex of said non-enzymatic glycosylated amino acids, peptides or mixtures thereof with said boronic acid;
   (b) separating the so-formed complex from said urine; and
   (c) analyzing the separated complexed material to establish the presence and amount of amino acids, peptides or mixtures thereof to obtain the complexed non-enzymatically glycosylated amino acid content of the urine, which content provides an indicia of blood glucose integrated over a period of time from about one week to about one month.

2. A method of monitoring blood glucose integrated over a period of time from about one week to about one month, by separating and quantitating non-enzymatic glycosylated amino acids, peptides or mixtures thereof present in the patient's urine, comprising:
  (a) contacting a urine sample containing said non-enzymatic glycosylated amino acids, peptides or mixtures thereof with a color dye reactive with amino acids so as to attach the dye to said non-enzymatic glycosulated amino acids, peptides or mixtures thereof;
  (b) treating the dye containing solution so produced with a suitable boronic acid to form a complex of said non-enzymatic glycosylated amino acids, peptides or mixtures thereof with such boronic acid;
  (c) separating the so-formed complex from said fluid; and
  (d) colorimetrically analyzing the separated, dyed, complexed material to establish the presence and amount of of amino acids, peptides or mixtures thereof to obtain the amino acid content of the urine, which content provides an indicia of blood glucose integrated over a period of from about one week to about one month.

3. The method according to claim 1 or 2, wherein said complex is formed under alkaline conditions.

4. The method according to claim 3, wherein said alkaline conditions comprise a pH of at least 9.

5. The method according to claim 1 or 2, wherein said boronic acid is immobilized on a support.

6. The method according to claim 1 or 2, wherein prior to analysis for amino acids, peptides or mixtures thereof the complex is treated with an acid.

7. The method according to claim 6, wherein said acid is HCl.

8. The method according to claim 1 or 2, wherein naturally occurring insoluble materials have been removed from the urine sample.

9. A method for monitoring metabolic control in a diabetes patient comprising measuring the amount of non-enzymatic glycosylated amino acids and peptides in the urine of the patient and comparing the measurement with a previously prepared standard showing non-enzymatic glycosylated amino acid and peptide content as a function of integrated blood glucose concentration.

10. The method according to claim 9, wherein the non-enzymatic glycosylated amino acids and peptides present in the urine of the patient are separated from the urine and quantitated.

11. The method according to claim 10, wherein the non-enzymatic glycosylated amino acids and peptides are separated from the urine by treatment with an insolubilized boronic acid so as to form an insoluble complex of said boronic acid and said non-enzymatic glycosylated amino acids and peptides; and separating said complex from the urine.

12. The method according to claim 11, wherein prior to complex formation, the insoluble materials present in the urine have been removed.

13. A test kit for the colorimetric determination of non-enzymatically glycosylated amino acids and/or peptides in a urine sample, comprising:
  (a) a predetermined amount of an insolubilized suitable boronic acid;
  (b) a predetermined amount of a color dye reactive with amino acids by attachment of the dye to said non-enzymatic glycosylated amino acids and/or peptides, whereby (a) and (b) are separated from one another by being placed in separate containers; and
  (c) previously prepared standards for colorimetric comparison.

14. The test kit according to claim 13, wherein the insolubilized boronic acid has been equilibrated with an alkaline buffer.

15. The test kit according to claim 13, wherein the color dye is an azo dye.

16. The test kit according to claim 13, wherein the color dye is dansyl chloride.

17. The test kit according to claim 13, wherein said boronic acid and said color dye are in separate packets such that a pH adjusted urine sample may be contacted with the color dye, brought into contact with said boronic acid, and the boronic acid can be washed free of the urine sample non-reacted dye.

18. The test kit according to claim 13, wherein said boronic acid is coated on a strip of a porous material.

19. The test kit according to claim 13, wherein said boronic acid is coated on an elongated cylindrical body comprising a porous material.

20. The test kit according to claim 18, wherein said strip of porous material is coated on only one side.

21. A test kit according to claim 13 or 18, and for the determination of said amino acids and/or peptides, wherein the color dye reactive with amino acids is present in an amount which is stoichiometrically in excess of that necessary to react with all of the amino acids present in the urine sample.

22. The test kit according to claim 21, wherein the insolubilized boronic acid is present in an amount which is stoichiometrically in excess of that necessary to form a complex with the non-enzymatic glycosylated amino acids and peptides present in the urine sample.

23. A test strip for the colorimetric detection of non-enzymatically glycosylated amino acids and/or peptides in a urine sample comprising a strip of porous material which has been at least partially coated with an insolubilized boronic acid and impregnated with a color dye reactive with amino acids by attachment of the dye to said nonenzymatic glycosylated amino acids and/or peptides.

24. A test strip according to claim 23, and for the determination of said amino acids and/or peptides, wherein the color dye reactive with amino acids is present in an amount which is stoichiometrically in excess of that necessary to react with all of the amino acids present in the urine sample.

25. The test strip according to claim 24, wherein the insolubilized boronic acid is present in an amount which is stoichiometrically in excess of that necessary to form a complex with the non-enzymatic glycosylated amino acids and peptides present in the urine sample.

26. The test strip according to claim 25, wherein the strip of porous material is paper.

* * * * *